United States Patent
Tang et al.

(10) Patent No.: US 10,675,308 B2
(45) Date of Patent: Jun. 9, 2020

(54) CHINESE MEDICINE EXTRACT AND PREPARATION METHOD AND APPLICATION THEREOF

(71) Applicant: INFINITUS (CHINA) COMPANY LTD., Jiang Men, Guangdong (CN)

(72) Inventors: Jian Tang, Guangdong (CN); Wenjuan Deng, Guangdong (CN); Guangrong Liu, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 188 days.

(21) Appl. No.: 15/561,178

(22) PCT Filed: Jun. 24, 2016

(86) PCT No.: PCT/CN2016/087100
§ 371 (c)(1),
(2) Date: Sep. 25, 2017

(87) PCT Pub. No.: WO2017/016355
PCT Pub. Date: Feb. 2, 2017

(65) Prior Publication Data
US 2018/0078584 A1    Mar. 22, 2018

(30) Foreign Application Priority Data
Jul. 30, 2015    (CN) .......................... 2015 1 0466544

(51) Int. Cl.
| | |
|---|---|
| *A61K 35/644* | (2015.01) |
| *A61Q 19/00* | (2006.01) |
| *A61K 36/282* | (2006.01) |
| *A61P 37/02* | (2006.01) |
| *A61P 17/00* | (2006.01) |
| *A61P 37/08* | (2006.01) |
| *A61K 8/9783* | (2017.01) |
| *A61K 8/98* | (2006.01) |

(52) U.S. Cl.
CPC .......... *A61K 35/644* (2013.01); *A61K 8/9783* (2017.08); *A61K 8/988* (2013.01); *A61K 36/282* (2013.01); *A61P 17/00* (2018.01); *A61P 37/02* (2018.01); *A61P 37/08* (2018.01); *A61Q 19/00* (2013.01); *A61K 2236/33* (2013.01); *A61K 2236/37* (2013.01)

(58) Field of Classification Search
None
See application file for complete search history.

(56) References Cited

FOREIGN PATENT DOCUMENTS

| | | | |
|---|---|---|---|
| CN | 1559403 A | | 1/2005 |
| CN | 101099547 A | | 1/2008 |
| CN | 101829246 A | * | 9/2010 |
| CN | 102784170 A | | 11/2012 |
| CN | 103535701 A | * | 1/2014 |
| CN | 104224849 A | | 12/2014 |
| CN | 105079064 A | | 11/2015 |
| KR | 101029534 B1 | | 4/2011 |
| KR | 20130135597 A | | 12/2013 |
| KR | 20140136260 A | | 11/2014 |
| KR | 20150033477 A | | 4/2015 |

OTHER PUBLICATIONS

Handa ("An Overview of Extraction Techniques for Medicinal and Aromatic Plants." Extraction Technologies for Medicinal and Aromatic Plants. Ed. Handa, Sukhdev S. Trieste: International Centre for Science and High Technology, 2008. 21-33).*
Pedraza-Alva et al., "Negative regulation of the inflammasome: keeping inflammation under control",Immunological Reviews, May 2015, vol. 265, p. 231-257.
Clinical and Experimental Dermatology, 2005, vol. 31, pp. 147-148.
First Office Action dated Aug. 7, 2018 for Japanese patent application No. 2017-556177, 3 pages, English translation provided by Global Dossier.
Database WPI Week 201104 Thomson Scientific, London, GB; AN 2010-N16071, XP002785145.
Database WPI Week 201544 Thomson Scientific, London, GB; AN 2015-23450E, XP002785146.
Database WPI Week 201416 Thomson Scientific, London, GB; AN 2013-X33842, XP002785147.
Database WPI Week 201504 Thomson Scientific, London, GB; AN 2014-W30253, XP002785148.
European Search Report dated Oct. 15, 2018 for European patent application No. 16829721.6, 8 pages.
International Search Report for PCT/CN2016/087100, dated Sep. 19, 2016, ISA/CN.
Wu, Xili et al., Effect of Artemisinin on the Expressions of GRα mRNA, GRβ mRNA and P300/CBP Protein in Lupus Nephritis Mice, Journal of Chinese Medicinal Materials, Apr. 30, 2012, pp. 608-612, vol. 35, No. 4, Journal of Chinese Medicinal Materials Bian Ji Bu, Guangzhou, Guangdong, China.
Yin, Hezi et al., Application of Propolis in Dermatology, Shanghai Journal of Traditional Chinese Medicine, Nov. 30, 1990, pp. 28-29, No. 11, Shanghai Journal of Traditional Chinese Medicine Bian Ji Bu, Shanghai, China
First Office Action dated Mar. 23, 2020 for Chinese patent application No. 201510466544.1, English translation provided by Global Dossier.

* cited by examiner

*Primary Examiner* — Susan Hoffman
(74) *Attorney, Agent, or Firm* — Yue (Robert) Xu; Apex Attorneys at Law, LLP

(57) ABSTRACT

A Chinese medicine extract and preparation method and application thereof. Raw materials of the extract are *Artemisia carvifolia* and propolis. The extract has an excellent effect of inhibiting CaN-NF-AT pathway and a lower relative toxicity for cells.

3 Claims, No Drawings

CHINESE MEDICINE EXTRACT AND PREPARATION METHOD AND APPLICATION THEREOF

The present application is a National Phase entry of PCT Application No. PCT/CN2016/087100, titled "CHINESE MEDICINE EXTRACT AND PREPARATION METHOD AND APPLICATION THEREOF", filed Jun. 24, 2016, which claims the priority of Chinese Patent Application No. 201510466544.1, as filed on Jul. 30, 2015 and titled with "CHINESE MEDICINE EXTRACT AND PREPARATION METHOD AND APPLICATION THEREOF", and the disclosures of both of which are incorporated herein by reference.

FIELD

The present invention relates to the field of traditional Chinese medicine, and in particular to a Chinese medicine extract, preparation method and use thereof.

BACKGROUND

Calcineurin (CaN), also called protein phosphatase 2B (PP2B), belongs to serine/threonine protein phosphatase family. Up to date, CaN is the only one serine/threonine protein phosphatase which is regulated by $Ca^{2+}$/calmodulin (CaM). CaN executes its functions through removing the phosphate from its substrates. In T cells, $Ca^{2+}$ influx increases intracellular $Ca^{2+}$ concentration, and then $Ca^{2+}$ binds to CaM and CaN, activates CaN. After activated CaN removes the phosphate from its substrate NF-AT, the substrates enter cell nucleus and activate the expression of some cytokines including IL-2. CaN-FN-AT pathway plays a key regulative role in T cells activation.

At present, calcineurin inhibitor is the most effective immunosuppressive agent in clinic. It is used in organ transplantation, the control of transplantation rejection and the treatment of autoimmune diseases (RA, CD, psoriasis). In particular, it has a satisfied effect on the treatments of skin allergic and skin inflammation (such as eczema) in recent years. As an immunosuppressive agent, calcineurin inhibitors (CNIs) are divided into exogenous inhibitors and endogenous protein inhibitors. Exogenous inhibitors include cyclosporine, tacrolimus, etc. Endogenous protein inhibitors include Cain, FKBP38, etc. To date, the most popular CNIs in clinic are ascomycin derivatives including cyclosporine A, tacrolimus and pimecrolimus. These inhibitors have similar physical-chemical properties, mechanisms and effects, but their toxicity and side-effect (such as nephrotoxicity, hyperglycaemia, etc.) are big barriers for their application. Therefore, finding more effective and safer calcineurin inhibitors, which target CaN-NF-AT pathway, is important in the new type skin inflammation drug development.

Chinese medicine is the traditional medicine in China, and in clinic, Chinese medicine shows fairly good effect on the treatments of skin inflammation (such as eczema) and autoimmune diseases. Recent research found that some active ingredients in Chinese medicine (such as quercetin, kaempferol, phenolic gossypol) can bind to CaN directly and inhibit its activity. Also, some active ingredients of Chinese medicine (such as cordycepin, farrerol, fisetin) can inhibit the activation of CaN-NF-AT pathway at the cellular level, thus inhibit the expression of type Th1 and Th2 cytokines as well as the activation of T cells. Chinese medicine has the properties of wide material source, low cost and low toxicity, so it should be widely used. Through reasonable Chinese medical formulas, Chinese medicine will have at least the same effect as Western medicine on the treatment of skin inflammation, and can be used in the cosmetics which have anti-allergic and skin relax function.

SUMMARY

In view of the above, the object of the present invention is to provide a Chinese medicine extract, preparation method and use thereof. The Chinese medicine extract provided in the present invention can block the CaN-NF-AT pathway effectively and as such function in the treatment of skin inflammation or autoimmune diseases, for example, eczema. Furthermore, the Chinese medicine extracts provided in the present invention have wide raw material source, simple preparation method and is suitable for large-scale production.

The Chinese medicine extract provided in the present invention is made from *Artemisia carvifolia* and propolis.

In an embodiment of the present invention, the mass ratio of *Artemisia carvifolia* to propolis is 3:5 to 5:3.

In some embodiments, the mass ratio of *Artemisia carvifolia* to propolis is 3:5.

In some embodiments, the mass ratio of *Artemisia carvifolia* to propolis is 5:3.

*Artemisia carvifolia* is the dry above-ground part of *Artemisia annua* L., which belongs to the Compositae family. *Artemisia carvifolia* contains various active ingredients including artemisinin, flavones and its analogs. *Artemisia carvifolia* has the functions of removing heatstroke and blocking malaria. It is used to treat heatstroke, Yin deficiency, night hot and morning cold, bone steaming, malaria, moist heat and jaundice.

Propolis is the yellow brown or black brown sticky materials secreted by Apidae family animals when they fix their honeycomb. It can be used as a Chinese medicine. The property of propolis is mild and the taste of propolis is bitter, spicy and a little bit sweet. Recent researches show that propolis contains rich flavones, amino acids, vitamins and organic acids. Propolis has the functions of keeping skin moisture, improving skin growth, diminishing inflammation and releasing pains. It can be used in the treatments of stomach ulcers, oral ulcers, burns, scalds, skin cracking and radiation protection.

In the present invention, the extract obtained from extracting the combination of *Artemisia carvifolia* and propolis can inhibit the CaN-NF-AT pathway effectively and has a much better effect than *Artemisia carvifolia* or propolis alone. Also, experiments indicate that the extract provided by the present invention has relatively low cell toxicity.

A method for preparing a Chinese medicine extract provided by the present invention comprises the extraction of *Artemisia carvifolia* and propolis.

In an embodiment of the present invention, the solvent for extraction is one of the group consisting of alcohols, alkanes, chloroform, acetone, water and ethyl acetate, or the mixture thereof.

In some embodiments, the alcohol is selected from the group consisting of ethanol, methanol, glycerol, butanediol, propylene glycol, pentylene glycol and hexylene glycol, or the mixture thereof.

In some embodiments, the alkane is methane, ethane or petroleum ether.

In some embodiments, the solvent for extraction is ethanol-water solution.

In some embodiments, the solvent for extraction is 95% (volume) ethanol in water.

In an embodiment of the present invention, extraction method is percolation, impregnation, decoction, reflux extraction, continuous extraction, supercritical fluid extraction or ultrasound extraction.

In an embodiment of the present invention, extraction temperature is room temperature, high temperature or intelligent temperature control; extraction pressure is vacuum, high pressure or constant pressure.

In an embodiment of the present invention, the preparation method of Chinese medicine extract provided in the present invention comprises: extract *Artemisia carvifolia* and propolis through percolation extraction by using ethanol-water solution as extraction solvent, and concentrate the filtered solution.

In some embodiments, by percolation extraction, the ethanol in the extraction solvent is 95% (volume).

In some embodiments, by percolation extraction, the mass of ethanol-water solution used is 20 to 30 folds of the sum of the mass of *Artemisia carvifolia* and propolis.

In some embodiments, by percolation extraction, the mass of ethanol-water solution is 20, 25 or 30 folds of the sum of the mass of *Artemisia carvifolia* and propolis.

In some embodiments, the duration by percolation extraction is 40 h-60 h.

In some embodiments, the duration by percolation extraction is 48 h.

In some embodiments, by percolation extraction, concentration is performed under low temperature and reduced pressure.

In some embodiments, by percolation extraction, the filtered solution is concentrated to the same mass as the sum of the mass of *Artemisia carvifolia* and propolis.

In an embodiment of the present invention, the preparation method of a Chinese medicine extract provided in the present invention comprises: extracting *Artemisia carvifolia* and propolis through percolation extraction by using methanol as an extraction solvent and concentrating the filtered extract solution.

In some embodiments, by percolation extraction, the amount of methanol is 30 folds of the sum of *Artemisia carvifolia* and propolis amount.

In some embodiments, the duration by percolation extraction is 48 h.

In some embodiments, by percolation extraction, the mass of concentrated filtered solution is the same as the sum of the mass of *Artemisia carvifolia* and propolis.

In an embodiment of the present invention, the preparation method of a Chinese medicine extract provided in the present invention comprises: extracting *Artemisia carvifolia* and propolis through continuous reflux extraction by using chloroform as an extraction solution and concentrating the filtered extract solution.

In some embodiments, by continuous reflux extraction, the mass of chloroform is 10 folds of the sum of the mass of *Artemisia carvifolia* and propolis.

In some embodiments, the duration by continuous reflux extraction is 24 h.

In some embodiments, by continuous reflux extraction, the mass of concentrated filtered solution is the same as the sum of the mass of *Artemisia carvifolia* and propolis.

In an embodiment of the present invention, the preparation method of a Chinese medicine extract provided in the present invention comprises: extracting *Artemisia carvifolia* and propolis through reflux extraction by using ethyl acetate as an extraction solution and concentrating the filtered extract solution.

In some embodiments, by continuous reflux extraction, the mass of ethyl acetate is 10 folds of the sum of the mass of *Artemisia carvifolia* and propolis.

In some embodiments, the duration by reflux extraction is 36 h.

In some embodiments, by reflux extraction, the mass of concentrated filtered solution is the same as the sum of the mass of *Artemisia carvifolia* and propolis.

In an embodiment of the present invention, the preparation method of Chinese medicine extract provided in the present invention comprises: extracting *Artemisia carvifolia* and propolis through ultrasound extraction by using butanediol or acetone as a solvent and concentrating the filtered extract solution.

In some embodiments, by ultrasound extraction, the mass of solvent is the same as the sum of the mass of *Artemisia carvifolia* and propolis.

In some embodiments, by ultrasound extraction, the temperature is 18° C.-25° C. and the duration is 1 h-3 h.

In some embodiments, by ultrasound extraction, the extract in solvent is adjusted to the same mass as the sum of the mass of *Artemisia carvifolia* and propolis.

In an embodiment of the present invention, the preparation method of a Chinese medicine extract provided in the present invention comprises: extracting *Artemisia carvifolia* and propolis through impregnation by using petroleum ether as an extraction solution and concentrating the filtered extract solution.

In some embodiments, by impregnation extraction, the mass of petroleum ether is 30 folds of the sum of the mass of *Artemisia carvifolia* and propolis.

In some embodiments, the duration by impregnation extraction is 48 h.

In some embodiments, by impregnation extraction, the mass of concentrated filtered solution is the same as the sum of the mass of *Artemisia carvifolia* and propolis.

In an embodiment of the present invention, the preparation method of a Chinese medicine extract provided in the present invention comprises: extracting *Artemisia carvifolia* and propolis through decoction extraction in water and concentrating the filtered extract solution.

In some embodiments, by decoction extraction, the mass of water is 30 folds of the sum of the mass of *Artemisia carvifolia* and propolis.

In some embodiments, by decoction extraction, the duration is 48 h and the temperature is 98° C.-105° C.

In some embodiments, the mass of concentrated filtered solution is the same as the sum of the mass of *Artemisia carvifolia* and propolis.

In an embodiment of the present invention, the preparation method of a Chinese medicine extract provided in the present invention comprises: extracting *Artemisia carvifolia* and propolis through supercritical fluid extraction by using ethanol as a cosolvent and concentrating the filtered extract solution.

In some embodiments, the mass of cosolvent is 30 folds of the sum of the mass of *Artemisia carvifolia* and propolis.

In some embodiments, the extraction pressure is 33 Mpa-35 Mpa, the extraction temperature is 50° C., duration is 48 h and the $CO_2$ flow rate is 15 L/h-25 L/h.

In some embodiments, the mass of concentrated filtered solution is the same as the sum of the mass of *Artemisia carvifolia* and propolis.

The preparation method of a Chinese medicine extract provided in the present invention is simple, easy to handle, no need for complex instruments and suitable for large-scale production.

The present invention provides a use of the Chinese medicine extract in the preparation of CaN-NF-AT pathway inhibitor.

In the present invention, experiment target is the activation of NF-AT gene in K562 cells which are induced by PMA and A23187. By using the Chinese medicine extract provided by the present invention as a test sample, experiment result demonstrates that the Chinese medicine extract provided by the present invention can inhibit the activation of CaN-NF-AT pathway effectively and the inhibition rate is up to 69.43%, which is significantly better than the use of *Artemisia carvifolia* or propolis alone. Because the Chinese medicine composition provided by the present invention can inhibit the CaN-NF-AT pathway dramatically, the extract can be used to treat diseases which target the CaN-NF-AT pathway.

The present invention provides a use of the Chinese medicine extract in the preparation of a medicament for skin inflammation or autoimmune diseases treatment.

Preferably, skin inflammation is eczema.

Preferably, autoimmune disease is RA, CD or psoriasis.

The present invention provides a medicament used for treating skin inflammation or autoimmune diseases, comprising the Chinese medicine extract provided by the present invention.

The dosage form of the medicament provided in the present invention to treat skin inflammation or autoimmune diseases is cream.

The present invention provides a use of a Chinese medicine extract in the preparation of cosmetic which has skin relax and anti-allergy function The present invention provides a cosmetic which has skin relax and anti-allergy function, comprising the Chinese medicine extract provided by the present invention.

The extract provided by the present invention, which is made from *Artemisia carvifolia* and propolis, can inhibit the CaN-NF-AT pathway effectively and has a better result than the use of *Artemisia carvifolia* or propolis alone. Also, experiment indicates that the extract provided by the present invention has a relative low toxicity to cells.

The preparation method of a Chinese medicine extract provided in the present invention is simple, easy to handle, no need for complex instruments and suitable for large-scale production.

DETAILED DESCRIPTION OF EMBODIMENTS

The present invention provides a Chinese medicine extract, preparation method and use thereof. One of ordinary skill in the art can use this disclosure for reference and improve the technological parameter to reach the same result. In particular, all similar replacements and changes are obvious for those of ordinary skill in the art, so they will be considered within the scope of the present invention. The method and use of the present invention have been described in preferred embodiment. It is apparent that others can achieve and apply the technology in the present invention through reasonable changes and combinations within the scope of the present invention, to implement and apply the techniques of the present invention.

The instruments and reagents used in the present invention are regular market products and commercial available.

Hereinafter, the present invention will be further described in conjunction with the examples:

Example 1

30 g *Artemisia carvifolia* and 50 g propolis were added to 20-fold mass of 95% ethanol and percolation extraction was performed for 48 h. The extract was obtained by collecting and concentrating the filtered solution to 80 g under low temperature and reduced pressure.

Example 2

30 g *Artemisia carvifolia* and 50 g propolis were added to 25-fold mass of 95% ethanol and percolation extraction was performed for 48 h. The extract was obtained by collecting and concentrating the filtered solution to 80 g under low temperature and reduced pressure.

Example 3

50 g *Artemisia carvifolia* and 30 g propolis were added to 30-fold mass of 95% ethanol and percolation extraction was performed for 48 h. The extract was obtained by collecting and concentrating the filtered solution to 80 g under low temperature and reduced pressure.

Example 4

50 g *Artemisia carvifolia* and 30 g propolis were added to 30-fold mass of methanol and percolation extraction was performed for 48 h. The extract was obtained by collecting and concentrating the filtered solution to 80 g under low temperature and reduced pressure.

Example 5

40 g *Artemisia carvifolia* and 40 g propolis were added to 10-fold mass of chloroform and continuous reflux extraction (Soxhlet extraction) was performed at room temperature for 24 h. The extract was obtained by collecting and concentrating the filtered solution to 80 g under low temperature and reduced pressure.

Example 6

35 g *Artemisia carvifolia* and 45 g propolis were added to 10-fold mass of ethyl acetate and reflux extraction was performed at room temperature for 36 h. The extract was obtained by collecting and concentrating the filtered solution to 80 g under low temperature and reduced pressure.

Example 7

50 g *Artemisia carvifolia* and 30 g propolis were added to the same mass of butanediol and ultrasound extraction was performed at room temperature for 2 h. The extract was obtained by collecting the filtered solution and adjusting the mass to 80 g in butanediol.

Example 8

50 g *Artemisia carvifolia* and 30 g propolis were added to the same amount of propanedione and ultrasound extraction was performed at 50° C. for 2 h. The extract was obtained by collecting the filtered solution and adjusting the mass to 80 g in propanedione.

Example 9

50 g *Artemisia carvifolia* and 30 g propolis were added to 30-fold mass of petroleum ether and impregnation extraction was performed at room temperature for 48 h. The extract was obtained by collecting and concentrating the filtered solution to 80 g under low temperature and reduced pressure.

Example 10

45 g *Artemisia carvifolia* and 35 g propolis were added to 30-fold mass of water and decoction extraction was performed for 48 h. The extract was obtained by collecting and concentrating the filtered solution to 80 g under low temperature and reduced pressure.

Example 11

30 g *Artemisia carvifolia* and 50 g propolis were used for supercritical fluid extraction under the conditions: pressure 33-35 MPa, temperature 50° C., time 3.5 h, $CO_2$ flow rate 15-25 L/h, ethanol volume rate in the cosolvent 15%. The extract was obtained by collecting and concentrating the solution to 80 g under low temperature and reduced pressure.

Comparative Example 1

80 g *Artemisia carvifolia* was added to 25-fold mass of 95% ethanol and percolation extraction was performed for 48 h. The extract was obtained by collecting and concentrating the filtered solution to 80 g under low temperature and reduced pressure.

Comparative Example 2

80 g propolis was added to 25-fold mass of 95% ethanol and percolation extraction was performed for 48 h. The extract was obtained by collecting and concentrating the filtered solution to 80 g under low temperature and reduced pressure.

Comparative Example 3

60 g *Artemisia carvifolia* and 20 g propolis were added to 25-fold mass of 95% ethanol and percolation extraction was performed for 48 h. The extract was obtained by collecting and concentrating the filtered solution to 80 g under low temperature and reduced pressure.

Comparative Example 4

20 g *Artemisia carvifolia* and 60 g propolis were added to 25-fold mass of 95% ethanol and percolation extraction was performed for 48 h. The extract was obtained by collecting and concentrating the filtered solution to 80 g under low temperature and reduced pressure.

Example 12

Test sample: all extracts were dissolved in 70% ethanol and diluted in deionized water to a working solution of 0.2 mg/ml. For detection, 10 μl sample, in which the final concentration of test extract is 0.2 mg/ml, was added to the test tube.

CaN enzyme activity test: CaN activity test kit from Enzo Life Science was used and the test was performed according to the manufacture's instruction on the kit. 25 μl CaM working solution, 5 μl CaN working solution and 10 μl 50 μM test sample working solution were added to a small centrifuge tube, mixed well and incubated at 30° C. for 10 minutes. In the control tube, 10 μl 0.5% DMSO water solution was added instead of test sample. After incubation, 10 μl substrate working solution was added to each tube and mixed well. After incubation at 30° C. for 50-60 minutes, 100 μl chromogenic reagent was added and mixed well. After standing for 20-30 minutes, 135 μl solution from each tube was transferred to a 96-well plate and subjected to absorbance measurement at 620 nm.

The determination of the optimum concentration of activator PMA and A23187: to determine the optimum concentrations of activator PMA and A23187 which activate the CaN-NF-AT pathway, PMA was added at concentration: 2.5 ng/ml, 5 ng/ml, 10 ng/ml, 20 ng/ml and 40 ng/ml. A23187 was added at concentration: 0.125 μM, 0.25 μM, 0.5 μM, 1 μM and 2 μM. Each concentration has 4 repeat wells. After activation for 18 h, fluorescence intensity from all experiment groups was detected at 1 μm.

Test method: NFAT K562 reporter stable cell line, in which the NFAT reporter gene was expressed constantly, was purchased from Affimatrix (U.S.A.). After K562 cells were treated with PMA (CPKC kinase activator) and A23187 (Calcium channel activator), the luciferase gene expression level, which was controlled by transcription factor NFAT, was detected. The expression level of luciferase reporter gene reflects the activation level of CaN pathway. Results were shown in table 1:

TABLE 1

The effects of PMA and A23187 to the expression of K562 NF-AT reporter gene at different concentrations

| Activator concentration | | Value at 1 μM | | | | |
|---|---|---|---|---|---|---|
| PMA ng/ml | A23187 μM | Well 1 | Well 2 | Well 3 | Well 4 | Average |
| 0 | 0 | 261 | 197 | 179 | 148 | 196 |
| 2.5 | 0.125 | 1165 | 1608 | 1128 | 1228 | 1282 |
| 5 | 0.25 | 1859 | 1708 | 1918 | 2163 | 1912 |
| 10 | 0.5 | 3228 | 2970 | 2368 | 2518 | 2771 |
| 20 | 1 | 2317 | 2963 | 2527 | 3278 | 2771 |
| 40 | 2 | 3332 | 2530 | 3780 | 3239 | 3220 |

As shown in table 1, PMA and A23187 can activate the expression of reporter gene at a dose-dependant manner. The difference of fluorescence readings between repeat wells can be controlled in a reasonable range. The optimum concentrations determined by above experiment for CaN pathway activators were: PMA 10 ng/ml, A23187 0.5 μM.

K562 cells in which the NFAT reporter gene was expressed constantly were conventional subcultured in RPMI-1640 medium with 10% fetal bovine serum. Healthy and logarithmic growth phase cells were used in the experiment. Cells were cultured in 24-well plate at a density of $2\times10^5$/well and treated with the extracts from example 1-3 and comparative example 1-5. The wells without extract were set as control group and the wells without PMA and A23187 were set as blank group. After one hour incubation, PMA (10 ng/ml) and A23187 (0.5 μM) (channel stimulants) were added to stimulate 18 h, then cells were collected and the fluorescence intensity (reflecting the activation level of CaN pathway in the cells) was detected at 1 μm by using the luciferase test kit according to the protocol.

The formula to calculate the inhibition ratio is: inhibition ratio (%) $W=[1-(X-A)/(B-A)] \times 100$.

Wherein, A is the average of blank at 1 μm, B is the average of control at 1 μm, X is the average of extract at 1 μm. Results were shown in table 2:

TABLE 2

The inhibition ratio of different samples to CaN-NF-AT pathway in K562 cells

|  | Inhibition ratio (%) |
| --- | --- |
| Example 1 | 66.58 |
| Example 2 | 68.97 |
| Example 3 | 69.43 |
| Comparative example 1 | 36.69 |
| Comparative example 2 | 42.37 |
| Comparative example 3 | 39.21 |
| Comparative example 4 | 45.46 |

As shown in table 2, both *Artemisia carvifolia* and propolis total flavonoids can inhibit the CaN-NF-AT pathway quite well. Using SPSS 19.0 version statistics software for analysis:

Example average±SED: 68.32%±1.53%;

Comparative example average±SED: 40.93%±3.81%.

By one-way ANOVA, the difference between examples and comparative examples are significant (P<0.01).

The result of statistic analysis indicated that the combination of *Artemisia carvifolia* and propolis has a much better effect than *Artemisia carvifolia* or propolis alone. Therefore, the formulas provided in the present invention have a better result on CaN-NF-AT pathway inhibition and can be used to treat diseases targeting CaN-NF-AT pathway, such as skin inflammation (eczema) and autoimmune diseases (RA, CD or psoriasis).

The extracts from other examples in the present invention have a similar inhibition ratio as the extracts from examples 1-3 and a significant difference compared to comparative examples 1-4.

Example 13

Test the cell toxicity of extracts from examples 1-3 and comparative examples 1-5 by regular CCK8 assay, comprising the steps of:

(1) 100 μl K562 cells suspension (1×10⁵/well) was placed into 96-well plate and preincubated in the incubator for 24 h (37° C., 5% $CO_2$);

(2) 10 μl extract from example 1-3 and comparative example 1-5 was added to the wells respectively except 6 control wells;

(3) 96-well plate was incubated in the incubator for 24 h;

(4) 10 μl CCK8 solution was added to each well;

(5) 96-well plate was incubated in the incubator for 4 h;

(6) The absorbance was measured in a microplate reader at 450 nm.

The formula to calculate the cell toxicity is: relative toxicity (%) $W=[(A-X)/A] \times 100$ Wherein, A is the average of blank $OD_{450}$, X is the average of extract $OD_{450}$. Results were shown in table 3:

TABLE 3

The relative cell toxicity of the extracts provided by the present invention

|  | Relative toxicity (%) |
| --- | --- |
| Example 1 | 2.9 |
| Example 2 | 3.1 |
| Example 3 | 3.3 |
| Comparative example 1 | 3.0 |
| Comparative example 2 | 3.2 |
| Comparative example 3 | 3.1 |
| Comparative example 4 | 3.2 |

The result indicated that there is no statistic difference between the cell toxicity of test samples. The relative cell toxicities were all quite low. Because the extract provided in the present invention was made from natural raw Chinese medicine, it overcomed the hidden dangers of Western medicine or hormone drug which has a pretty big side-effect. This extract provided a material base for the anti-eczema and skin relax cosmetics.

The extracts from other examples in the present invention have a similar relative cell toxicity as the extracts from examples 1-3 or comparative examples 1-4.

Above embodiments are only the preferred embodiments in the present invention. What needs to be pointed out is: one of ordinary skill in the art can make modification and improvement within the scope of the present invention; these modification and improvement shall be under the protection scope of the present invention.

The invention claimed is:

1. A method for preparing a Traditional Chinese medicine extract, comprising extracting the raw materials consisting of *Artemisia* carvifolia and propolis, wherein the mass ratio of *Artemisia* carvifolia to propolis is 3:5 to 5:3.

2. The method according to claim 1, wherein a solvent for extraction is one of the group consisting of alcohols, alkanes, chloroform, acetone, water and ethyl acetate, or a mixture thereof.

3. The method according to claim 1, wherein the extraction method is percolation, impregnation, decoction, reflux extraction, continuous reflux extraction, supercritical fluid extraction or ultrasound extraction.

\* \* \* \* \*